(12) United States Patent
Liu et al.

(10) Patent No.: US 10,105,293 B2
(45) Date of Patent: Oct. 23, 2018

(54) CORE-SHELL PARTICLE

(71) Applicants: AGENCY FOR SCIENCE, TECHNOLOGY AND RESEARCH, Singapore (SG); THE PROCTER & GAMBLE COMPANY, Singapore (SG)

(72) Inventors: Ye Liu, Singapore (SG); Guan Wang, Singapore (SG); Robert Wayne Glenn, Jr., Liberty Township, OH (US); Saurabh Gupta, Singapore (SG); Todd Underiner, Cincinnati, OH (US)

(73) Assignees: AGENCY FOR SCIENCE, TECHNOLOGY AND RESEARCH, Singapore (SG); THE PROCTER & GAMBLE COMPANY, Singapore (SG)

( * ) Notice: Subject to any disclaimer, the term of this patent is extended or adjusted under 35 U.S.C. 154(b) by 0 days.

(21) Appl. No.: 15/465,670

(22) Filed: Mar. 22, 2017

(65) Prior Publication Data
US 2017/0273875 A1   Sep. 28, 2017

Related U.S. Application Data

(60) Provisional application No. 62/311,530, filed on Mar. 22, 2016.

(51) Int. Cl.
*A61K 8/02* (2006.01)
*A61K 8/90* (2006.01)
*A61K 8/58* (2006.01)
*A61K 9/50* (2006.01)
*A61Q 5/00* (2006.01)

(52) U.S. Cl.
CPC .......... *A61K 8/0245* (2013.01); *A61K 8/0241* (2013.01); *A61K 8/0258* (2013.01); *A61K 8/0287* (2013.01); *A61K 8/585* (2013.01); *A61K 8/90* (2013.01); *A61K 9/5031* (2013.01); *A61K 9/5089* (2013.01); *A61Q 5/00* (2013.01); *A61K 2800/412* (2013.01); *A61K 2800/56* (2013.01); *A61K 2800/652* (2013.01)

(58) Field of Classification Search
CPC ... A61K 8/0287; A61K 8/0241; A61K 8/0258
See application file for complete search history.

(56) References Cited

PUBLICATIONS

Kumar et al, "Recent Advancement in Functional Core-Shell Nanoparticles of Polymers, Synthesis,Physical Properties, and Applications in Medical Technology", Journal of Nanoparticles, vol. 2013, Article ID 672059, 24 pages. 2013.*

* cited by examiner

*Primary Examiner* — Carlos A Azpuru

(57) ABSTRACT

There is provided a core-shell particle comprising a polymer conjugate encapsulating an active agent, wherein the polymer conjugate comprises a biocompatible polymer and a polyacidic polymer. There is also provided a process for forming the core-shell particle, a delivery vehicle comprising the core-shell particle and a method for delivering an active agent to a desired site.

22 Claims, 9 Drawing Sheets

1

CORE-SHELL PARTICLE

TECHNICAL FIELD

The present invention generally relates to a core-shell particle. The present invention also relates to a process for forming a core-shell particle.

BACKGROUND ART

Encapsulation and delivery systems are important for many applications in consumer care and health care. A good encapsulation and delivery system should have 1) a good stability to achieve a long shelf life for storage and good integrity for drug delivery before reaching target sites, 2) stealth layers to provide a good dispersity in aqueous solution and targeting capability, and 3) a suitable fluidity for release of species encapsulated at target sites when needed. For some application, higher deposition efficiency is additionally required.

However, one the most formidable challenges in developing qualified encapsulation and delivery system is to address the dilemma between stability and fluidity of vesicles. A system with a good fluidity always has a poor stability. For example, liposomes obtained from self-assembly of amphiphilic lipids are dynamic and feasible for spices to move into and out, but the stability of liposomes are poor due to the weak interaction among short hydrophobic lipid segments which is responsible for the integrity of liposomes. Cross-linking or formation of polymer based or silica cages can stabilize liposomes but also reduce the fluidity. In comparison, the structures and properties of polymer vesicles formed by self-assembly of amphiphilic copolymers can be adjusted in a wider range through tuning the chemistry, composition and molecular weight of copolymers. Several polymeric formulations have been provided basically utilizing synthetic emulsifier such as polysorbate materials or glycerin fatty acid esters for delivery of dietary supplement Coenzyme O10. In addition, block copolymer of polyethylene glycol and poly propylene glycol have been applied for encapsulation and delivery of active ingredients. However, these systems cannot achieve the required balance between stability and fluidity.

In addition, should it be desired to deliver a fluidic active agent such as silicone oil to a site, the silicone oil is usually chemically altered to improve the deposition of the silicone oil. Silicone oil is usually used in hair products, fabric care and detergents. However, the chemical modification of the silicone oil may result in other undesired side effects such as sticky feeling and accumulation of the chemically modified silicone oil.

Therefore, it is attractive to develop stimuli-responsive encapsulation and delivery systems which can encapsulate the species securely, but also be able to release the species under stimuli which can be pH, thermal and redox etc, and without any undesirable side effects. Several types of pH responsive vesicles have been reported, such as pH-responsive PMAA-g-hollow silica vesicles and polymer complexes coated hollow silica vesicles. However, the formulations of these systems are not straightforward and can be cumbersome. In addition, the loading processes cannot be performed easily. In some cases, the loading of certain active ingredients cannot be realized or have a low loading efficiency and loading content. These limit the applications that can be used for such delivery systems.

There is a need to provide a core-shell particle that overcomes, or at least ameliorates, one or more of the disadvantages described above.

SUMMARY OF INVENTION

According to a first aspect, there is provided a core-shell particle comprising a polymer conjugate encapsulating an active agent, wherein said polymer conjugate comprises a biocompatible polymer and a polyacidic polymer.

Advantageously, the core-shell particle may encapsulate the active agent within the core of the particle at a first pH and then release the active agent from the core of the particle at a second pH. Hence, the core-shell particle may act as a delivery vehicle which is sensitive to pH changes.

Advantageously, the core-shell particle may be stable due to the conjugation between the biocompatible polymer and the polyacidic polymer.

According to a second aspect, there is provided a process for forming a core-shell particle comprising a polymer conjugate encapsulating an active agent, wherein said polymer conjugate comprises a biocompatible polymer and a polyacidic polymer, the process comprising the steps of (a) providing a mixture comprising said biocompatible polymer, said polyacidic polymer and said active agent in an acidic environment; and (b) drying said mixture to obtain said core-shell particle.

Advantageously, the biocompatible polymer may self-assemble in the presence of the polyacid polymer in the acidic environment to form the core-shell particle, wherein the shell is hydrophilic. While self-assembling, the biocompatible polymer sequesters and encapsulates the active agent such that the active agent is within the core of the particle.

According to a third aspect, there is provided a delivery vehicle comprising the core-shell particle as described herein, wherein the core-shell particle releases the active agent from the core when the particle is at a neutral pH.

As the core-shell particle is formed in an acidic environment, when the pH of the core-shell particle is increased, the core-shell particle may disassemble and release the active agent from the core.

According to a fourth aspect, there is provided a method for delivering an active agent to a desired site comprising the steps of (a) providing the core-shell particle of any one of statements 1 to 21 in an acidic environment; and (b) increasing the pH of said core-shell particle to thereby release and deliver said active agent.

Definitions

The following words and terms used herein shall have the meaning indicated:

The term 'biocompatible polymer' is to be interpreted broadly to include a polymer that does not present any toxicity to a mammal in the amount used. The biocompatible polymer may be substantially non-immunogenic when used internally in a mammal patient. The biocompatible polymer may be substantially insoluble in blood or in a tissue.

The term 'polyacidic polymer' is to be interpreted broadly to include a polymer that has at least one acidic functional group in the side chain or at the terminal end of the polymer, and includes the ester or anhydride of the acid. The acidic functional group may be a carboxylic acid group, a thiol group, a sulfonic acid group or a sulphonamide group.

The term "active agent" is to be interpreted broadly to include a chemical material or compound suitable for administration to a mammal and that induces a desired beneficial effect, e.g., exhibits a desired pharmacological activity. The active agent may be administered to a surface or hair of a mammal (topical administration), or may be introduced into a mammal through oral administration, inhalation, injection or intravenous administration, etc. The term includes, for example, agents that are therapeutically effective, prophylactically effective, and cosmetically (and cosmeceutically) effective. There are also included derivatives and analogs of those compounds or classes of compounds specifically mentioned which also induce the desired beneficial effect.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a core-shell particle will now be disclosed.

The core-shell may comprise a polymer conjugate encapsulating an active agent, wherein the polymer conjugate comprises a biocompatible polymer and a polyacidic polymer.

In the core-shell particle, the biocompatible polymer may be an amphiphilic polymer. The amphiphilic polymer may be a block co-polymer comprising at least one hydrophobic polymer block and at least one hydrophilic polymer block. The hydrophilic polymer block may form the shell of the core-shell particle and the hydrophobic polymer block may form the core of the core-shell particle. Advantageously, due to the physical cross-linking between the hydrophilic polymer (forming the shell of the core-shell particle) and the polyacidic polymer, the polymer conjugate may be stable and may be capable of encapsulating the active agent within the core of the particle. The biocompatible polymer and the polyacid polymer may form the polymer conjugate via hydrogen bonding.

The biocompatible polymer may comprise monomers selected from the group consisting of halogenated alkylene, ether, sulfonated ether, alkylene, ketone, sulfone, alkylene oxide, urethane, acetate, alcohol, carbonate, lactone, lactide, glycolide, ester, anhydride, acrylate, pyrrolidone, saccharide and combinations thereof. The biocompatible polymer may be selected from the group consisting of polyvinylchloride, polytetrafluoroethylene, polyethersulfone, polyethylene, polyetheretherketone, polysulfone, polypropylene, poly(ethylene glycol), poly(propylene glycol), polyurethanes, ethylene vinyl acetate copolymers, collagen, poly isobutylene, ethylene vinyl alcohol copolymers, polyethylene polycarbonate, poly-ε-caprolactone, polylactide, polyglycolide, carbomers, polyesters, polyethers, polyanhydrides, polyacrylates, polyvinyl acetates, polyvinyl pyrrolidones, polysaccharides (such as hyaluronic acid, hydroxyalkylcelluloses, carboxyalkylcelluloses, or derivatives thereof), polyether, derivatives thereof and combinations thereof.

In one embodiment, the amphiphilic polymer may contain a poly(alkylene oxide) segment. The poly(alkylene oxide) may be poly(ethylene glycol) and hence the amphiphilic polymer may contain poly(ethylene glycol). The hydrophobic polymer may contain saturated or unsaturated carbon hydrogen chains. The hydrophobic polymer may be poly (propylene oxide) or poly(butyl methacrylate). Thus, the poly(ethylene glycol)-containing polymer may be a copolymer of poly(ethylene glycol)-poly(propylene glycol), a poloxamer, polyoxyethylene stearate or polysorbate.

The amphiphilic polymer may be commercially available polymers such as those from the Pluronics™ series (for the poly(ethylene glycol)-poly(propylene glycol) copolymer) or the Tween series (for the polysorbate).

In the core-shell particle, the polyacidic polymer may be selected from the group consisting of alginic acid, polysulfonamide, polypeptide, poly(carboxylic acid), polycarboxylate and combinations thereof. The polypeptide may be poly(aspartic acid) or poly(glutamic acid). The poly(carboxylic acid) may be selected from the group consisting of poly(acrylic acid), poly(methacrylic acid), poly(2-ethylacrylic acid) and poly(2-propylacrylic acid). The polyacidic polymer may function to stabilize the polymer conjugate.

In the core-shell particle, the active agent may be a fluidic active agent or a particulate active agent. The active agent may be encapsulated in the core of the core-shell particle. The active agent may generally be hydrophobic for encapsulation in the (hydrophobic) core. Where the active agent is a fluidic active agent, the fluidic active agent may be silicone oil. Where the active agent is a particulate active agent, the particulate active agent may be selected from the group consisting of a therapeutic agent, a cosmetic agent and a cosmoceutical agent. The particulate active agent may be an inorganic compound, a peptide, a drug (such as a small molecule drug, or a nucleic-acid based drug), a protein, an antibody, an antimicrobial agent or an herbicide.

The active agent may be loaded into the core of the core-shell particle at a loading concentration of from about 1% to about 80%, about 1% to about 10%, about 1% to about 20%, about 1% to about 30%, about 1% to about 40%, about 1% to about 50%, about 1% to about 60%, about 1% to about 70%, about 10% to about 80%, about 20% to about 80%, about 30% to about 80%, about 40% to about 80%, about 50% to about 80%, about 60% to about 80%, or about 70% to about 80%.

The core-shell particle may have a particle size in the nano-size range or the micro-size range. The core-shell particles can be spherical, non-spherical, tabular, plate-like, or irregular in shape. The core-shell particle may have a particle size in the range of about 10 nm to about 10,000 nm, about 200 nm to about 5,000 nm, about 100 nm to about 10,000 nm, about 500 nm to about 10,000 nm, about 1,000 nm to about 10,000 nm, about 2,500 nm to about 10,000 nm, about 5,000 nm to about 10,000 nm, about 7,500 nm to about 10,000 nm, about 10 nm to about 100 nm, about 10 nm to about 500 nm, about 10 nm to about 1,000 nm, about 10 nm to about 2,500 nm, about 10 nm to about 5,000 nm, or about 10 nm to about 7,500 nm. Where the core-shell particle is a sphere, the above particle size may refer to the diameter of the particle. Where the core-shell particle is not a sphere, the above particle size may refer to the equivalent spherical diameter of the particle.

In the core-shell particle, the biocompatible polymer and the polyacidic polymer may be in a respective polymers unit molar ratio of from 100:90 to 100:0.1.

The biocompatible polymer may cross-link with the polyacidic polymer. The crosslinking density of the cross-linked polymers may be at about least 5%, at least about 10%, or at least about 15%. The crosslinking density may be determined based on the molar ratio of the repeating units of the polyacidic polymer to the hydrophilic polymer.

The shell of the core-shell particle may at least partially encapsulate the core, or may completely encapsulate the core. The shell may be porous or may be a dense shell.

Exemplary, non-limiting embodiments of a process for forming a core-shell particle will now be disclosed. The core-shell particle may comprise a polymer conjugate encapsulating an active agent, wherein the polymer conjugate comprises a biocompatible polymer and a polyacidic polymer. The process may comprise the steps of (a) providing a mixture comprising the biocompatible polymer or monomers thereof, the polyacidic polymer or salt thereof and the active agent in an acidic environment; and (b) drying the mixture to obtain the core-shell particle.

The biocompatible polymer may self-assemble in the presence of the polyacidic polymer and the acidic environment to form the core-shell particle. As the biocompatible polymer self-assembles, it is able to sequester and encapsulate the active agent within the core of the particle.

The biocompatible polymer may be an amphiphilic block co-polymer comprising at least one hydrophobic polymer block and at least one hydrophilic polymer block. Hence, the monomer of the biocompatible polymer may be defined as either the hydrophobic polymer block or the hydrophilic polymer block. The polymer conjugate may be formed by mixing the hydrophobic polymer block and the hydrophilic polymer block with the salt form of the polyacidic polymer (where the cation is an alkali metal) or directly with the polyacidic polymer. Alternatively, the monomer of the biocompatible polymer may not be a polymer and may refer to either a hydrophobic monomer (which then binds to other hydrophobic monomers to form a hydrophobic polymer) or hydrophilic monomer (which then binds to other hydrophilic monomers to form a hydrophilic polymer). Here, the polymer conjugate may be formed by mixing the hydrophobic monomer and the hydrophilic monomer (in sufficient amounts to form the biocompatible polymer) with the salt form of the polyacidic polymer, or directly with the polyacidic polymer. Still alternatively, the polyacidic polymer or salt form thereof may be mixed directly with the formed biocompatible polymer and allowed to cross-link with the biocompatible polymer.

In step (a), the mixture may be provided in an aqueous environment. Where an organic solvent (such as for example tetrahydrofuran, dimethyl sulfoxide, or dimethylformamide) is used to dissolve the various components (biocompatible polymer or monomers thereof, or polyacidic polymer or salt thereof), the organic solvent may be removed and replaced with an aqueous solvent (such as water) through known methods such as dialysis or evaporation. The organic solvent stated above is only exemplarily and any organic solvent can be used, as long as it is able to dissolve the biocompatible polymer (or monomers thereof) or the active agent.

The various components of the mixture may be mixed via melt mixing. Here, the individual component or the various components of the mixture may be heated to a temperature above its/their melting point and then blended together. The blend may be dispersed in an aqueous solvent, such as water.

The various components such as the hydrophobic polymer block and the hydrophilic polymer block may be subjected to emulsifying or homogenizing to form the core-shell particle.

The acidic environment may be at a pH lower than the pKa of the polyacidic polymer. Hence the pH used in the acidic environment is dependent on the polyacid polymer used and its pKa. For example, the pH can be less than 7.5, less than 7, or about 6. The pKa of the polyacidic polymer used can be determined easily by the person skilled in the art.

In step (b), the drying step may involve the evaporation of water which can be carried out by heating, freeze drying or vacuum drying. The drying step may include spray drying.

There is also provided a delivery vehicle comprising the core-shell particle as described herein, wherein the core-shell particle releases the active agent from the core when the particle is at a pH higher than the pKa of the polyacidic polymers. It can be about 7.5, higher than 6 or higher than 7.0, as relevant depending on the polyacidic polymer used and its pKa. The release of the active agent may be sustained over a period of time. The release of the active agent may be a controlled release since the release can be triggered by altering the pH of the medium containing the core-shell particle.

There is also provided a method for delivering an active agent to a desired site comprising the steps of: (a) providing the core-shell particle as described herein in an acidic environment; and (b) increasing the pH of the core-shell particle to thereby release and deliver the active agent. The desired site may be the hair or surface of an animal.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

EXAMPLES

Figure 1:
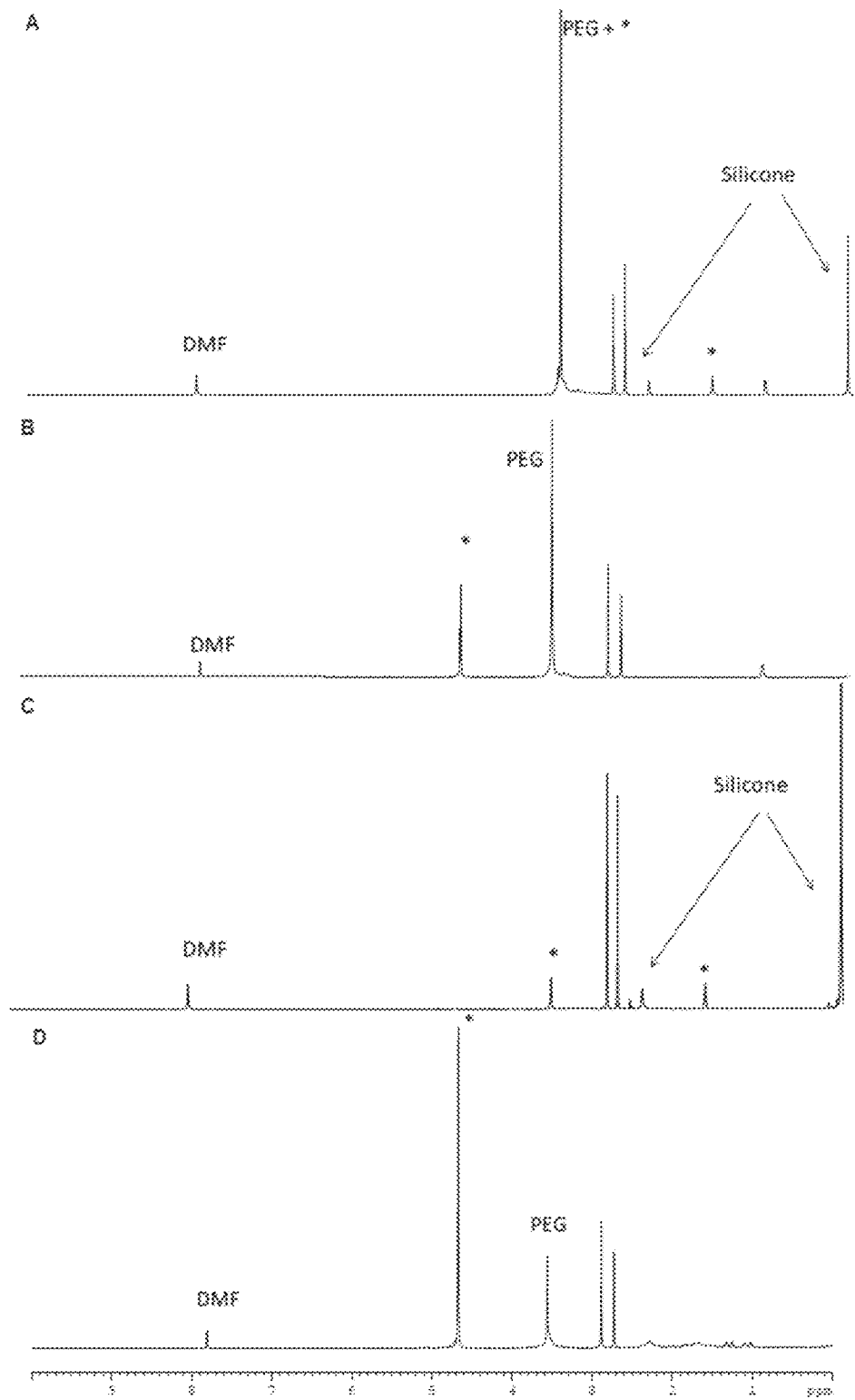
FIG. 1 is a 1H NMR spectra of A) Silicone-Pluronic polymer micelles in THF-D8; B) Silicone-Pluronic polymer micelles in deionized water; C) 20 mg of silicone oil in THF-D8; D) Silicone-Pluronic-PAA polymer complexes by adding PAA at the ratio of 1:1 in D20; E) CoQ10-Pluronic polymer micelles from Comparative Example 3; F) CoQ10-Pluronic polymer complexes by adding PAA at 1:1 ratio from Example 5; G) CoQ10-Tween 80 polymer micelles from Comparative Example 4; H) CoQ10-Tween 80 polymer complexes by adding PAA at 1:1 ratio from Example 6. (The * indicate the THF-D8 or deionized water solvent peaks)
Figure 1:
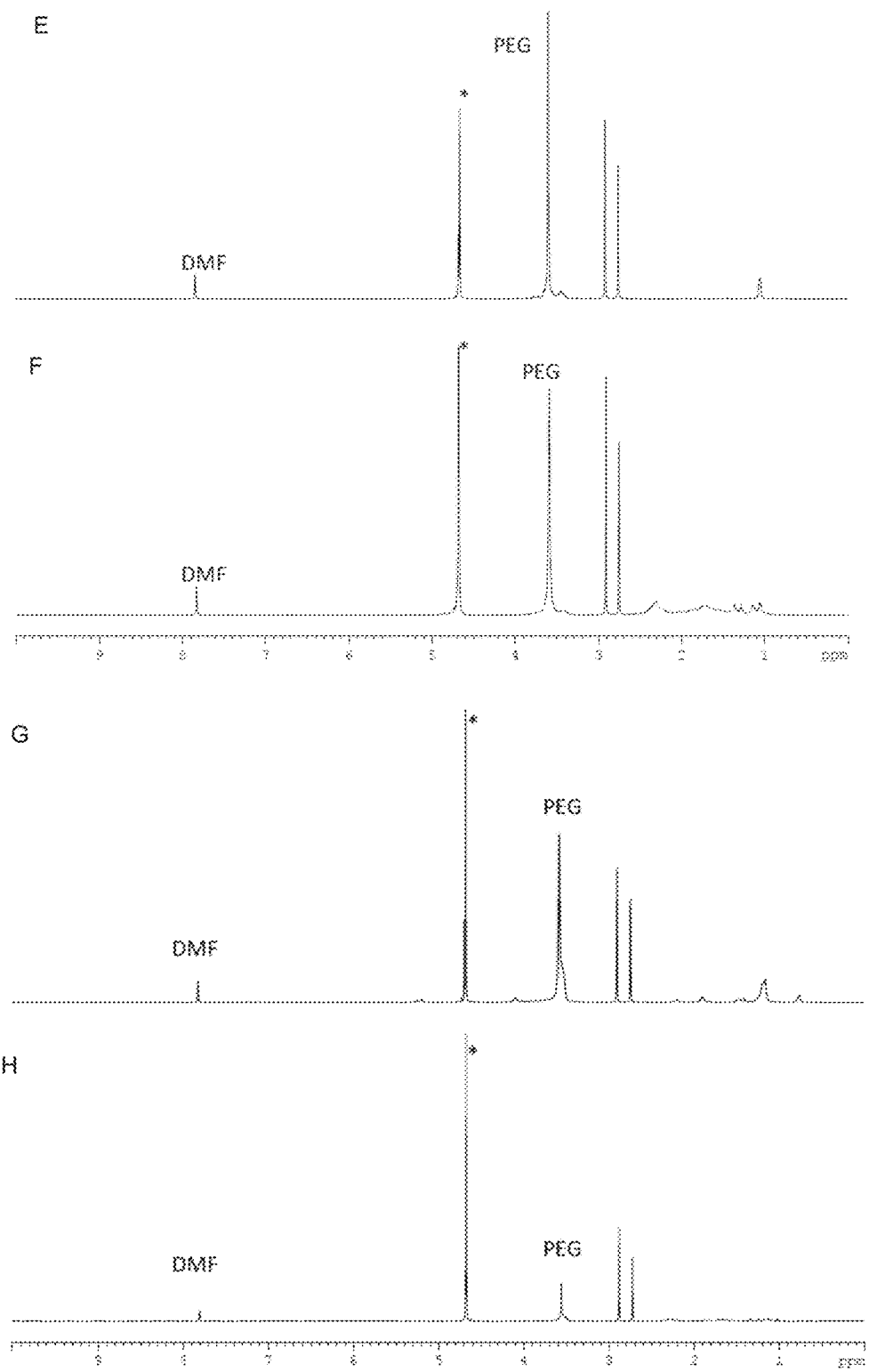

Non-limiting examples of the invention and comparative examples will be further described in greater detail by reference to specific Examples, which should not be construed as in any way limiting the scope of the invention.

Materials

Pluronic™ F108, Pluronic™ F127, Pluronic™ F68, Tween 80 and citric acid (food grade) were obtained from Sigma-Aldrich of St. Louis, Mo. of the United States of America. Polyacrylic acid was obtained from Polysciences, Inc of Warrington, Pa. of the United States of America and used as a 50% aqueous solution. Sodium polyacrylate (food grade) was obtained from Shijiazhuang Sinca Foods Co., Ltd of Shijiazhuang of China. Y-14945 Amino Silicone Fluid was obtained from Waterford Plant of New York of the United States of America. Coenzyme Q10 (CoQ10) was obtained from International Laboratory USA of South San Francisco, Calif. of the United States of America.

P&G VT2510 is a liquid mixture of 25-30% sodium alkyl sulphate (25-30% aqueous solution, CAS number 68585-47-7, 7732-18-5), 25-30% of distilled water (CAS number 7732-18-5), 20-25% of sodium laureth-3-sulfate (25-30% aqueous solution, CAS number 9004-82-4, 7732-18-5), 6-8% of Amphosol HCA-B, 6-8% of Celvol Polyvinyl Alcohol 523, 2-4% of glycerine (CAS number 56-81-5) and 2-4% of MIRAPOL AT-1.

EXAMPLES 1 to 9 AND COMPARATIVE EXAMPLES 1 to 7

Examples 1 to 9 and Comparative Examples 1 to 7 were produced according to the Methods below with reference to Table 1 which shows the amount of the various materials used.

Methods

To form the product of Examples 1 to 4 and Examples 7 to 9, the specific amount of the Pluronic™ polymer was mixed with the requisite amount of the Y-14945 amino silicone fluid and mixed in 20 mL of deionized water. The mixture was then homogenized using a high shear mixture (Ultra Turrax T18 basic homogenizer) until a fine homogeneous emulsion was obtained. The requisite amount of polyacrylic acid (PAA) was then added to the homogeneous emulsion and the emulsion was emulsified for an additional 5 minutes. The pH of the emulsion was about 5.5. The final emulsion was further freeze dried to obtain a white powder. The cross-linking degree is then calculated (based on molar ratio of the repeating units of PAA to PEG that is present in the Pluronic) and shown in Table 1.

To form the product in Comparative Examples 1, 2 and 5 to 7, the specific amount of the Pluronic™ polymer was mixed with the requisite amount of the Y-14945 amino silicone fluid and mixed in 20 mL of deionized water. The mixture was then homogenized using a high shear mixture (Ultra Turrax T18 basic homogenizer) until a fine homogeneous emulsion was obtained. The pH of the emulsion was about 7.0. The emulsion was then freeze dried to obtain an off white powder.

To form the product in Examples 5 and 6, the specific amount of the Pluronic™ or Tween 80 polymer and the requisite amount of the CoQ10 were melted and blended. After cooling down to room temperature, a yellowish paste was obtained. To the yellowish paste, 20 mL of deionized water was added and the mixture was homogenized using a high shear mixer until a fine homogeneous emulsion was obtained. The requisite amount of sodium polyacrylate was then added to this emulsion and the emulsion was emulsified for an additional 5 minutes. Citric acid was dissolved in the emulsion while stirring to achieve an emulsion with a pH of about 6. The final emulsion was further freeze dried to obtain a yellowish powder. The cross linking degree is then calculated (based on molar ratio of the repeating units of PAA to PEG that is present in the Pluronic/Tween) and shown in Table 1.

To form the product in Comparative Examples 3 and 4, the specific amount of the Pluronic™ polymer and the requisite amount of the CoQ10 were melted and blended. After cooling down to room temperature, a yellowish paste was obtained. To the yellowish paste, 20 mL of deionized water was added and the mixture was homogenized using a high shear mixer until a fine homogeneous emulsion was obtained. The pH of the emulsion was about 7.0. This emulsion was further freeze dried to obtain a yellowish powder.

When forming the polymer conjugate of Examples 1 to 9, the PEG from the Pluronic or the Tween form hydrogen bonding with the PAA. As shown above, PAA can be added directly or formed from sodium PAA. Water soluble PAA was added to the aqueous solution of capsules of block copolymer consisting of ethylene glycol units to form the complex with the PEG shells. The complex of PAA and PEG may alternatively be formed by adding sodium PAA to the aqueous solution of capsules of block copolymer of ethylene glycol and poly(propylene glycol) following by adjusting the pH to be acidic or by direct addition of PAA. The cross-linking degree is described by the molar ratio of the repeating units of PAA to PEG.

with a molar ratio of the repeating units PEG to that of PAA at 1:1 in deionized water. The ratio of the integral intensity of the peaks at ~3.5 ppm ascribed to the PEG to the peaks at ~7.8 ppm from DMF is reduced from 26.6 (shown in FIG. 1B) to 9.4 after formation of the complex between PEG and PAA. The ratio of the integral intensity of the peaks at ~2.3 ppm attributed to the PAA to that of external standard DMF is 3.4, lower than 13.3 without formation of complexes between PAA.

The loading of the silicone in Silicone-Pluronic-PAA complexes could be measured with 1H NMR spectroscopy with DMF as an external standard. The loading of the silicone was completed before the PAA was added. The 1H NMR spectrum in FIG. 1C showed an integration ratio of 20 for the peaks at ~0.1 ppm attributed to silicone to the peak at ~7.8 ppm for DMF for 20 mg of silicon in THF-D8. In

TABLE 1

| Material | Ex. 1 | Ex. 2 | Comp. Ex. 1 | Ex. 3 | Ex. 4 | Comp. Ex. 2 | Ex. 5 | Comp. Ex. 3 | Ex. 6 | Comp. Ex. 4 | Ex. 7 | Comp. Ex. 5 | Ex. 8 | Comp. Ex. 6 | Ex. 9 | Comp. Ex. 7 |
|---|---|---|---|---|---|---|---|---|---|---|---|---|---|---|---|---|
| Pluronic™ F108 (g) | 2 | 2 | 2 | | | | 2 | 2 | | | 1 | 1 | 0.8 | 0.8 | | |
| Pluronic™ F127 (g) | | | | 2 | 2 | 2 | | | | | 1 | 1 | 1.2 | 1.2 | | |
| Pluronic™ F68 (g) | | | | | | | | | | | | | | | 2 | 2 |
| Tween 80 (g) | | | | | | | | | 2 | 2 | | | | | | |
| Polyacrylic acid (g) | 0.3 | 0.45 | 0 | 0.3 | 0.45 | | | | | | 0.3 | | 0.3 | | 0.3 | |
| Y-14945 Amino Silicone Fluid (g) | 0.86 | 0.86 | 0.86 | 0.86 | 0.86 | 0.86 | | | | | 0.86 | 0.86 | 0.86 | 0.86 | 0.86 | 0.86 |
| Coenzyme Q10 (g) | | | | | | | 0.2 | 0.2 | 0.2 | 0.2 | | | | | | |
| Sodium polyacrylate | | | | | | | 0.3 | | 0.15 | | | | | | | |
| Cross-linking degree | ~9% | ~15% | 0 | ~9% | ~15% | 0 | ~8% | 0 | ~8% | 0 | ~9% | 0 | ~9% | 0 | ~9% | 0 |

Ex. refers to example.
Comp. Ex. refers to comparative example.

Characterization of Samples
Nuclear Magnetic Resonance

The structure of the sample was investigated using a 1H NMR (Bruker DPX 400 MHz NMR spectrometer). 1H NMR spectra of silicone loaded Pluronic F108 (Comparative Example 1) in tetrahydrofuran-D8 (THF-D8) and in deionized water are shown in FIGS. 1A and 1B with dimethylformamide (DMF) as an external reference. As both Pluronic F108 and silicone could be dissolved in THF-D8, the peaks at ~3.5 ppm attributed to the PEG from Pluronic F108 and the peaks at ~0.1 ppm and 2.5 ppm attributed to protons from silicone could be seen from FIG. 1A. However, in FIG. 1B, the peaks from silicone disappear. These results clearly show that the silicone oil was encapsulated in the hydrophobic cores of the micelle.

The loading of the silicone could be measured with 1H NMR spectroscopy with DMF as an external standard. FIG. 1C shows the 1H NMR spectrum for 20 mg of silicone in THF-D8. The peak at ~0.1 ppm attributed to silicone has an integration ratio of 20 to the peak at ~7.8 ppm for DMF. While in FIG. 1A, the peak at ~0.1 ppm shows an integration ratio of 4.6 to the peak at ~7.8 ppm, which indicates that the amount of silicone is 4.6 mg in a total weight of 19 mg of silicone-Pluronic samples. As a result, the calculated loading of silicone encapsulated is 24 wt %.

Figure 2:
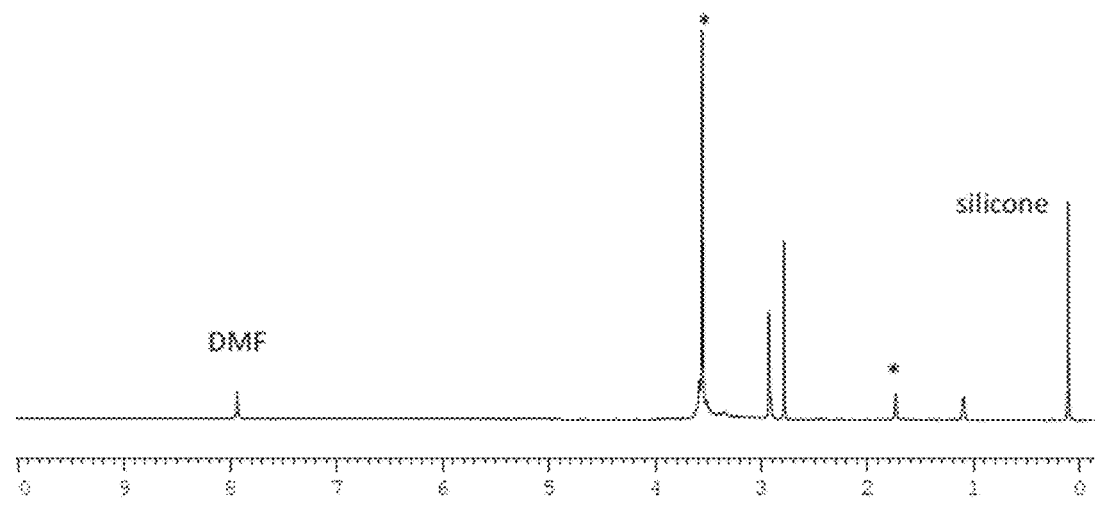
FIG. 2 is a 1H NMR spectra of Silicone-Pluronic-PAA complexes from Example 1 in THF-D8 (The * indicate the THF-D8 solvent peaks).

FIG. 1D shows 1H NMR spectrum of silicone loaded Pluronic F108 micelles after forming complex with PAA FIG. 2, the peak at ~0.1 ppm showed an integration ratio of 5 to the peak at ~7.8 ppm, which indicated that the amount of silicone is 5 mg in a total weight of 20 mg of Silicone-Pluronic-PAA complex sample. The calculated loading of silicone encapsulated is 25 wt %.

FIG. 1E shows 1H NMR spectrum of Q10 loaded Pluronic F108 (Comparative Example 3) in deionized water together with DMF as an external reference. The characteristic peaks of protons attributed to polypropylene oxide (from the Pluronic) at about 1.1 ppm almost disappeared in comparison with the characteristic peaks of protons attributed to PEG at about 3.5 ppm. The peaks attributed to CoQ10 totally cannot be observed. This shows that the CoQ10 was loaded in the hydrophobic polypropylene oxide portion, which has very low access to water. Therefore, it can be concluded that the formed core-shell particle (in the form of capsule) have PEG shells and cores composed of CoQ10 and polypropylene oxide.

FIG. 1F shows the 1H NMR spectra of CoQ10 loaded Pluronic F108 micelles after forming polymer complexes with PAA (from Example 5). The molar ratio of the repeating unit of PEG and PAA is 1:1. The ratio of the integral intensity of the peaks at 3.6 ppm attributed to the PEG to the peak of the external reference DMF at 7.8 ppm drops from 22 to 11 after forming complex with PAA. If no complex were formed, the ratio of the integral intensity of the peaks at 2.3 ppm attributed to PAA to the external reference DMF at 7.8 ppm should be 11:1. However, the ratio is around 3.2:1. These results reflect that the mobility of the PEG and PAA are reduced due to the formation of complex via hydrogen bonding. The complex formed should be gel-like with certain mobility in aqueous solution so that peaks attributed to PEG and PAA still appear.

FIG. 1G shows 1H NMR spectrum of CoQ10 loaded Tween 80 (from Comparative Example 4) in deionized water together with DMF as an external reference. The characteristic peaks at about 3.5 ppm were ascribed to PEG protons and the peaks at about 1 to 2 ppm were attributed to the alkyl chain protons from Tween 80. The very low intensity of alkyl chain protons indicated the formation of micelles which embedded the hydrophobic chains into the core of the micelles. In addition, the peaks attributed to CoQ10 totally cannot be observed, indicating that the CoQ10 was loaded in the hydrophobic core together with the alkyl chains in the micelles.

FIG. 1H shows the 1H NMR spectrum of Q10 loaded Tween micelles after formation of complexes with PAA at a molar ratio of the repeating units of PEG to that of PAA at 1:1 (from Example 6) in deionized water. As compared to FIG. 1G, the ratio of the integral intensities of the peaks at ~3.5 ppm (PEG peaks) to the peak at ~7.8 ppm (DMF peak) had decreased from 21 to 7.7, which showed the formation of complex between the PEG and PAA through hydrogen bonding. The ratio of the integral intensity of the peaks at ~2.3 ppm attributed to the PAA to the peaks at ~7.8 pm (DMF peaks) is 2.3, which should be 10.5 if no complex was formed.

Dynamic Light Scattering

Dynamic Laser Light Scattering (DLS, Brookhaven BIS200 laser light scattering system) was used to characterise the particle size of the silicone-Pluronic micelles in solution. Here, the light source is a power adjustable vertically polarized 35 mW argon ion laser with a wavelength of 633 nm. The scattering angle was fixed at 90° for measuring the hydrodynamic radius (Rh) and the average scattering intensity. Rh values were obtained using a CONTIN analysis.

Figure 3:
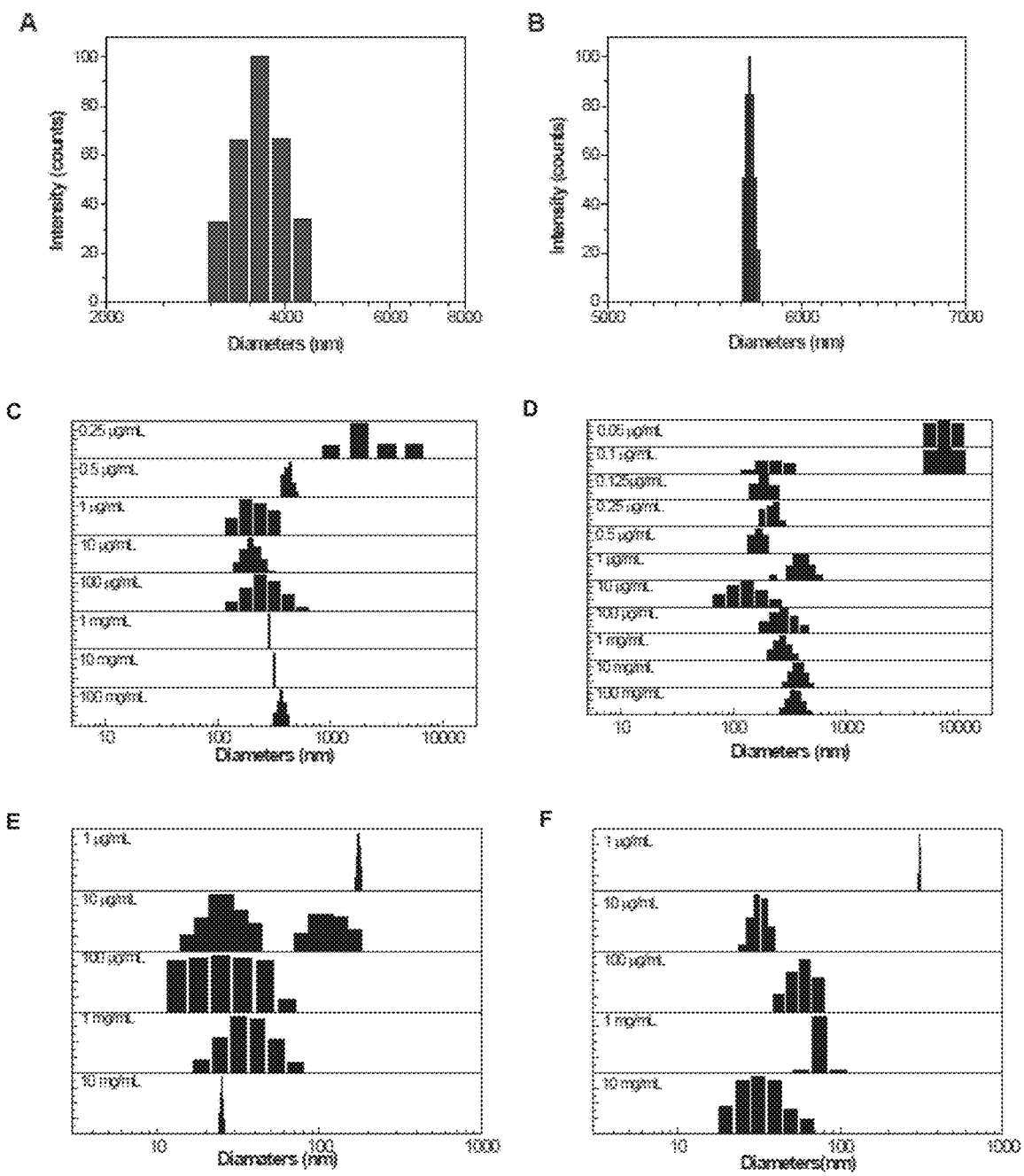
FIG. 3 is a measurement of the particle sizes by Dynamic Light Scattering (DLS) technique of the A) Silicone-Pluronic emulsion of Comparative Example 1; B) Silicone-Pluronic-PAA complexes emulsion of Example 1; C) CoQ10-Pluronic emulsion of Comparative Example 3; D) CoQ10-Pluronic-PAA complexes emulsion of Example 5; E) CoQ10-Tween 80 emulsion of Comparative Example 4; and F) CoQ10-Tween 80-PAA complexes emulsion of Example 6.

Referring to FIG. 3A, DLS showed that the average particle size of the micelles from Comparative Example 1 is about 3.5 µm, while FIG. 3B showed that the average particle size of the micelles from Example 1 is about 5.7 µm.

FIG. 3C and FIG. 3D show the dependence of the size on the concentration of CoQ10 loaded Pluronic F108 (Comparative Example 3) and CoQ10 loaded Pluronic F108 crosslinked with PAA (Example 5). The diameter of the CoQ10 loaded Pluronic F108 and CoQ10 loaded Pluronic F108 crosslinked with PAA is about 300 nm, which is kept to be almost constant when the concentration is higher than 0.5 µg/mL. When the solution was diluted further to 0.25 µg/mL, the CoQ10 loaded Pluronic F108 assemblies became unstable and disassembled to form a bigger aggregate, which could be ascribed as the clusters of CoQ10 formed. However, for the CoQ10 loaded Pluronic F108 crosslinked with PAA sample, the assemblies of a diameter of 300 nm were still stable when the concentration was reduced to 0.125 µg/mL (which is even lower than that concentration which caused the non-crosslinked sample to dissociate). Hence, the presence of the PAA that formed crosslinks with the PEG aided to stabilise the sample.

FIG. 3E and FIG. 3F show the dependence of the size on the concentration of CoQ10 loaded Tween (Comparative Example 4) and CoQ10 loaded Tween crosslinked with PAA (Example 6). The diameter of the CoQ10 loaded Tween and CoQ10 loaded Tween crosslinked with PAA is about 20 to 50 nm in the concentration between 10 mg/mL to 100 µg/mL. When the solution was diluted further to 10 µg/mL, the CoQ10 loaded Tween assemblies became unstable and started to disassemble and completely disassembled with the concentration was 1µg/mL. The large particle sizes observed were ascribed to the formation of the hydrophobic CoQ10 clusters. However, for the CoQ10 loaded Tween crosslinked with PAA sample, the assemblies were still stable when the concentration was reduced to 10 µg/mL. Hence, the presence of the PAA that formed crosslinks with the PEG aided to stabilise the sample.

Energy-Dispersive X-Ray Spectroscopy-Scanning Transmission Electron Microscopy (EDX-STEM)

Figure 4:
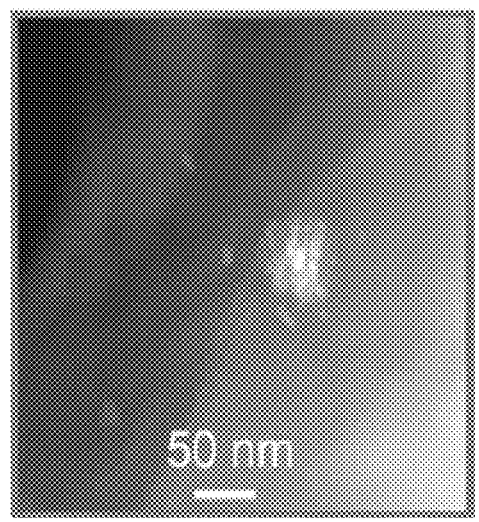
FIG. 4 is an Energy-dispersive X-ray spectroscopy-scanning transmission electron microscopy (EDX-STEM) image at a scale bar of 50 nm showing the silicone loaded Pluronic F108 (Example 1).

EDX-STEM was used to investigate the distribution of silicone in Pluronic. EDX analysis of the samples was acquired in STEM mode at an equal acquisition time, with a nominal electron beam diameter of 1 nm for the measurement; no beam damage or contamination was observed during the experiments. FIG. 4 shows EDX-STEM image of silicone loaded Pluronic F108 (Example 1) with a cross-linking degree of 9%. The silicon domains can be observed clearly in the matrix of Pluronic F108, and the diameter is about 50 nm.

Confocal Microscopy

The swelling process of the silicone (tagged with Rodamine B) loaded Pluronic F108 samples with and without cross-linking were monitored using confocal microscopy. Confocal images were taken under a confocal laser scanning microscope (CLSM, FV1000, Olympus, Japan).

Figure 5:
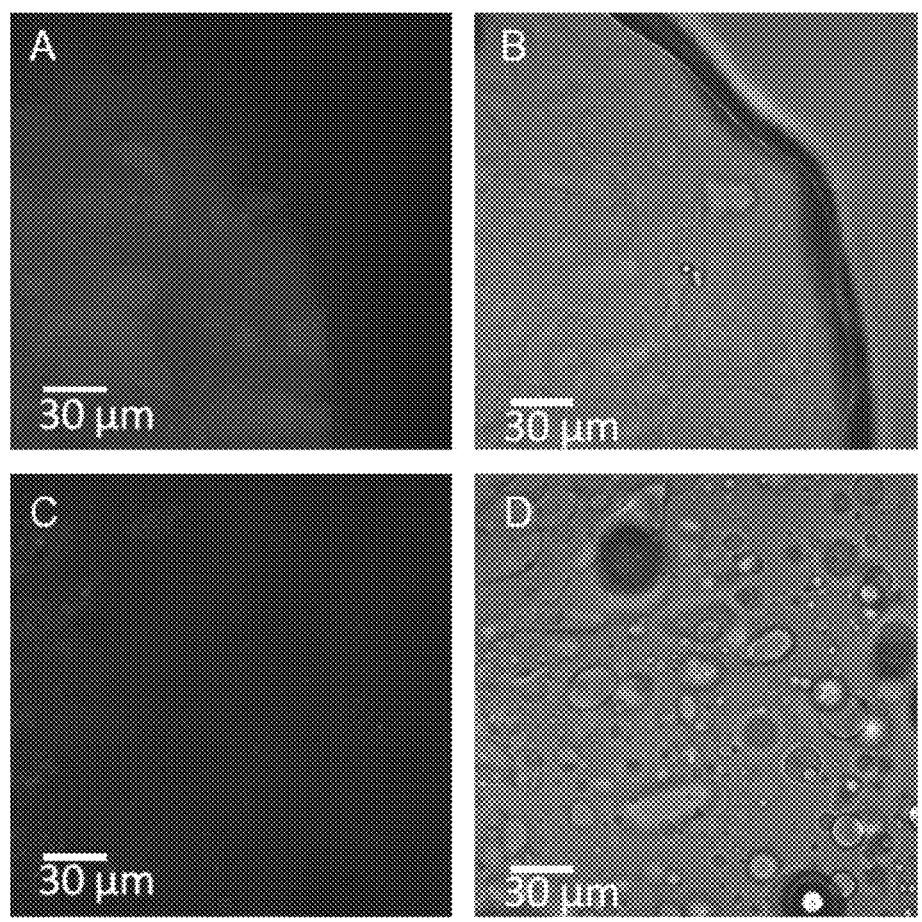
FIG. 5 is a number of confocal microscopy images of swollen silicone loaded Pluronic F108 samples of A) Example 1, fluorescent image; B) Example 1, bright field image; C) Comparative Example 1, fluorescent image; and D) Comparative Example 1, bright field image. All images were taken with a scale bar of 30 μm.

FIG. 5A and FIG. 5B show the swelling process of the sample with 9% cross-linking (Example 1) while FIG. 5C and FIG. 5D show the swelling process of the sample without cross-linking (Comparative Example 1) after some water was added. FIG. 5A and FIG. 5C are fluorescent images while FIG. 5B and FIG. 5D are the bright field images. It is clear that the swelling of the samples with cross-linking (from Example 1) was slower with gel formed as shown in FIG. 5A. In contrast, the sample without cross-linking (from Comparative Example 1) dissolved quickly. Hence, this showed that the presence of the PAA which cross-links with the PEG from the Pluronic aided in the slow dissolution of the sample. Thus, the presence of the PAA increased the stability of the sample.

Transmission Electron Microscopy (TEM)

Figure 6:
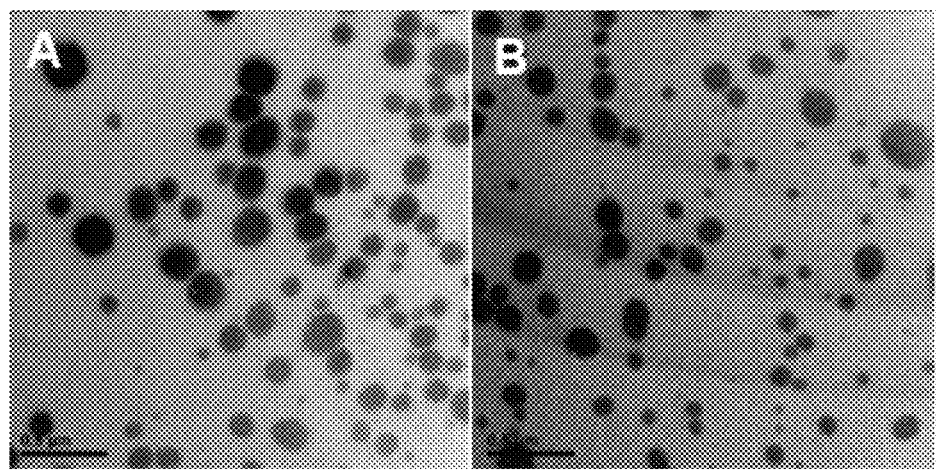
FIG. 6 is a number of Transmission Electron Microscopy (TEM) images of dried particles in A) CoQ10-Pluronic emulsion of Comparative Example 3; and B) CoQ10-Pluronic-PAA complexes emulsion of Example 5.

Transmission electron microscopy (TEM) was used to observe the particle morphology of the samples. The TEM images were obtained using a high resolution Philips CM300 transmission electron microscopy (FEGTEM) at 300 kV and the samples were prepared by dripping micelle solution onto a copper grid cover with carbon followed by drying in a desiccator. FIG. 6A shows TEM image of CoQ10 loaded Pluronic F108 (Comparative Example 3) while FIG. 6B shows TEM image of CoQ10 loaded Pluronic F108 crosslinked with PAA (Example 5). It can be seen that the particles formed are of spherical shapes with diameters from about 200 nm.

High Performance Liquid Chromatography (HPLC)

HPLC was used to determine the loading concentration of CoQ10. A Waters Alliance 2695 HPLC system equipped with a Waters 2420 UV detector and an analytical column (X-Bridge RP 18, 5µm, 150 mm×4 mm, Waters Corporation, Singapore) was used. The samples were eluted with acetonitrile (HPLC Grade, VWR Singapore) at a flow rate of 1 mL/min and CoQ10 was detected at 275 nm. The freeze dried powers from Examples 5 and 6 and Comparative Examples 6 and 7 were dissolved in a mixed solvent of water (in which the Pluronic™ and polyacrylic polymers can be dissolved) and hexane (in which CoQ10 can be dissolved). The hexane solutions of CoQ10 were then measured with HPLC.

The measured loading concentration of CoQ10 in Pluronic (from Comparative Example 3) was 9% while that from Pluronic-PAA complex (from Example 5) was 8%.

The measured loading concentration of CoQ10 in Tween 80 (from Comparative Example 4) was 8% while that from Tween 80-PAA complex (from Example 6) was 8%.

Release Profile

The release profile of amino-silicone from the sample was investigated in a dissolution medium, which contains 44.728 g of P&G VT2510 premix and 2 L of ultrapure water Typically, 160 g of this dissolution medium was pre-heated to about 40° C. into a 250 mL beaker on a magnetic stirrer hot plate. Samples from Example 1 and Comparative Example 1 that correlate to 250 ppm of amino-silicone in the medium were added to the medium. Extract aliquots of approximately 1 mL of dissolution medium at specific time intervals of 2, 15, 30, 60, 120, 300 and 600 seconds were withdrawn out through a 10 μm filter using a peristaltic pump into pre-labelled 4 mL VWR glass vials. Each aliquot was diluted with another 4 mL of the dissolution medium and sent for analysis using ICP-OES.

Figure 7:
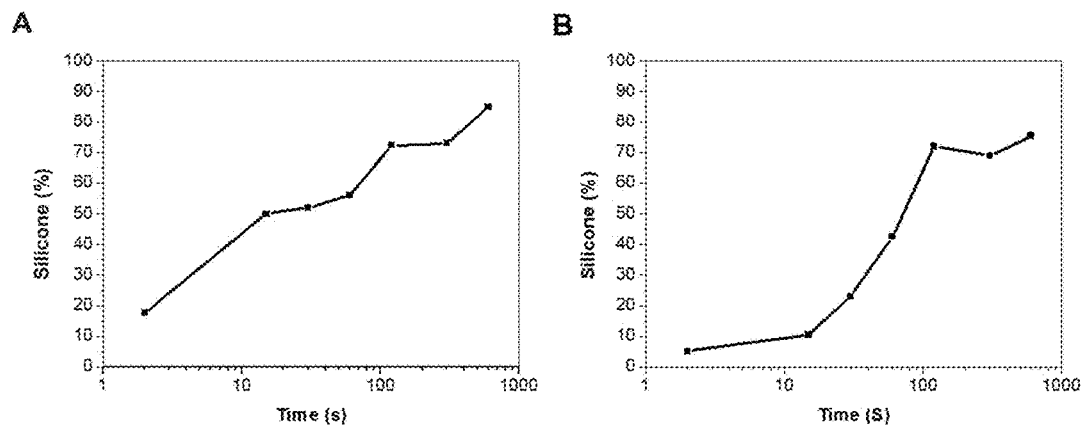
FIG. 7 is a graph showing the release profile of A) Pluronic F108-silicone sample in Comparative Example 1; and B) Pluronic F108-silicone-PAA sample in Example 1.

FIG. 7A and FIG. 7B show the release profiles of Comparative Example 1 and Example 1 respectively. The release of silicone from Example 1 was obviously delayed as compared to that from Comparative Example 1. The release percentage was delayed from 50% at 30 seconds and 56% at 60 seconds to 23% at 30 seconds and 42% at 60 seconds.

Deposition on Hair

The deposition of aminosilicone on hair (virgin and low lift) was conducted by 3 circles. Powder samples from Examples 1 to 3 and Comparative Example 1, which contain 0.012 g of silicone, were mixed in the palm of one hand in conjunction with 0.22 g of shampoo. Water at 37° C. was added into the center of the sample and the product was sheared using fingers from the other hand into liquid lather with about 10 strokes. The produce was then applied by coating hands to switches of 1.5 g, 6 inches long virgin hairs, which were treated with a shampoo (such as Global Wash from Procter & Gamble) and thoroughly wetted using 37° C. water for 20 seconds from top down. The hairs were then cleaned for 30 seconds to continue to work the shampoo into hairs. The hairs were rinsed with water for 30 seconds and excess water was gently squeezed off the hairs. Three legs of hairs were treated with 3 cycles individually before sending the treated hairs to a 50% RH/21° C. room to equilibrate overnight. 1 g of the hair switches were cut off from each equilibrated hair switch and sent for silicone analysis using ICP.

The deposition results of silicone on virgin and low-lift hair are summarised in Table 2. The non cross-linked sample from Comparative Example 1 showed deposition of 92±24 ppm on virgin hair, while the deposition is 204±30 ppm and 511±65 ppm for samples from Example 1 and Example 2 respectively. The deposition for sample from Example 3 showed a deposition of 701±1020 ppm on virgin hair. These data indicate that the cross-linking did have a positive effect on deposition of silicone onto virgin hair. In addition, the sample from Example 3 (based on Pluronic F127) had better deposition as compared to that from Example 1 (based on Pluronic F108).

On low-lift hair, the deposition for Comparative Example 1 was 0 ppm, while the depositions for Examples 1 to 3 were 8±1 ppm, 24±4 ppm and 22±5 ppm respectively. Although the deposition onto low lift hair was improved for samples with cross linking as compared to the sample without cross-linking, the deposition was much lower as compared to the virgin hair.

TABLE 2

|  |  | Comp. Ex. 1 | Ex. 1 | Ex. 2 | Ex. 3 | Control |
|---|---|---|---|---|---|---|
| Deposition | Deposition—virgin (ppm) | 92 ± 24 | 204 ± 30 | 511 ± 65 | 701 ± 1020 | 0 |
|  | Deposition—low lift hair (ppm) | 0 | 8 ± 1 | 24 ± 4 | 22 ± 5 | 0 |

Figure 8:
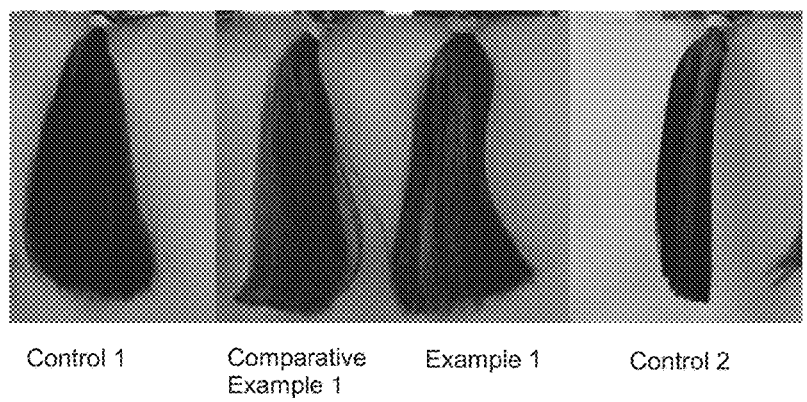
FIG. 8 is a number of images showing virgin hair treated with samples from Comparative Example 1 and Example 1. Control 1 is hair treated with silicone emulsion and Control 2 is hair treated with silicone containing a cationic deposition aid.

FIG. 8 is a picture comparing virgin hair treated with Comparative Example 1 and Example 1 with those treated with control 1 (silicone emulsion) and control 2 (silicone samples with cationic deposition aid). The hairs treated with Comparative Example 1 and Example 1 were more smooth than control 1 indicating the effective deposition of silicone onto the hair. However, the hair treated with control 2 were weighed down after wash, which is due to the bad effect of cationic deposition aid.

Rheology Study

Rheology study was conducted on TA instruments (Discovery HR-2). Samples from Examples 1 to 4 and Comparative Examples 1 and 2 were preparing with the dissolution medium used in the release profile characterization. The samples were also measured by direct mixing with the P&G VT2510 Premix. A frequency sweep was conducted at 5 Pa from a frequency of 0.01 to a frequency of 200 Hz or from an angular frequency of 0.1 to 100 rad/s. A flow sweep was conducted from a shear rate of 0.001 to 1000 $s^1$. The temperature was set at 25° C.

Figure 9:
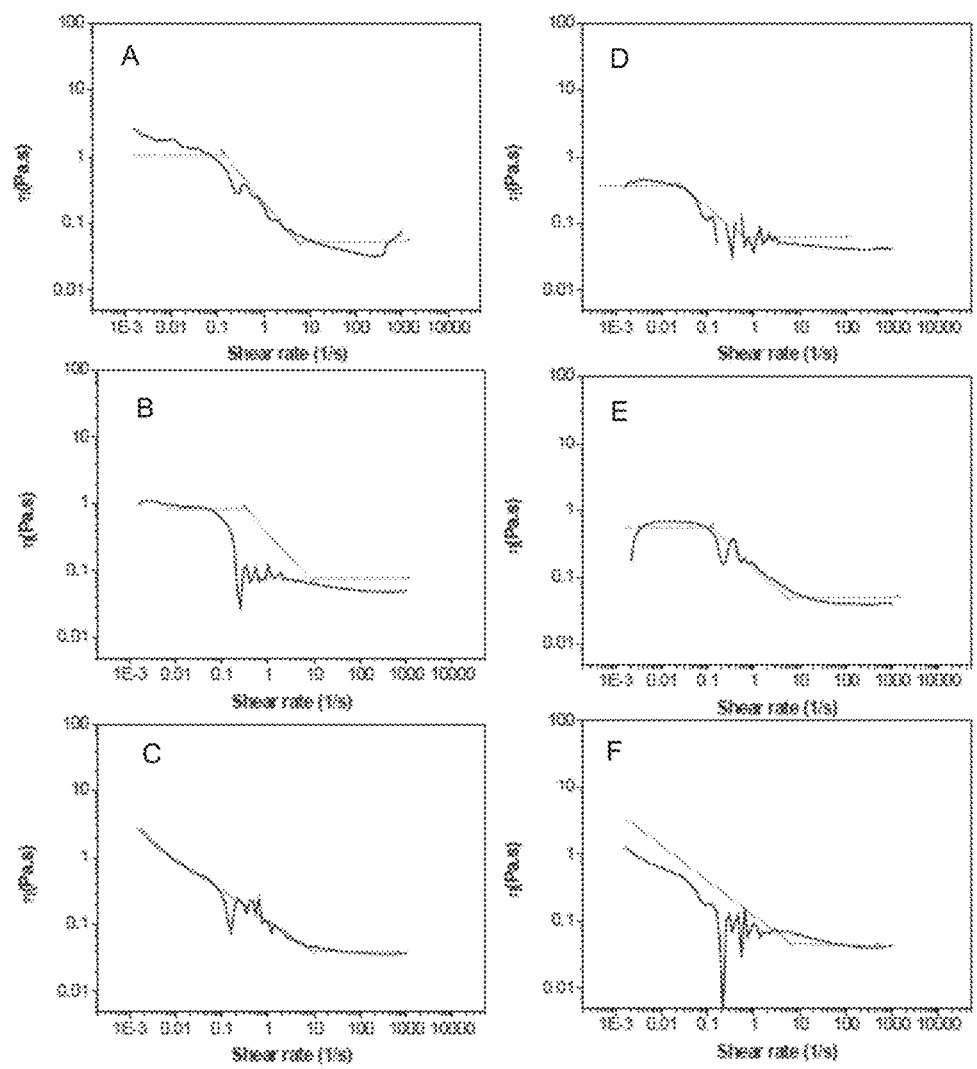
FIG. 9 is a number of graphs showing the shear thinning behaviours of A) Comparative Example 1; B) Example 1; C) Example 2; D) Comparative Example 2; E) Example 3 and F) Example 4.

The viscosity of samples from Examples 1 to 4 and Comparative Examples 1 and 2 were measured when dissolved into the dissolution medium. All samples showed shear thinning behaviours. As can be seen from FIG. 9, both initial and final plateau can be observed for Comparative Examples 1 and 2 (FIG. 9A and FIG. 9D respectively) and Examples 1 and 3 (FIG. 9B and FIG. 9E respectively).

However, the final plateau was observed for Examples 2 and 4 (FIG. 9C and FIG. 9F respectively), which have higher cross-linking content.

Figure 10:
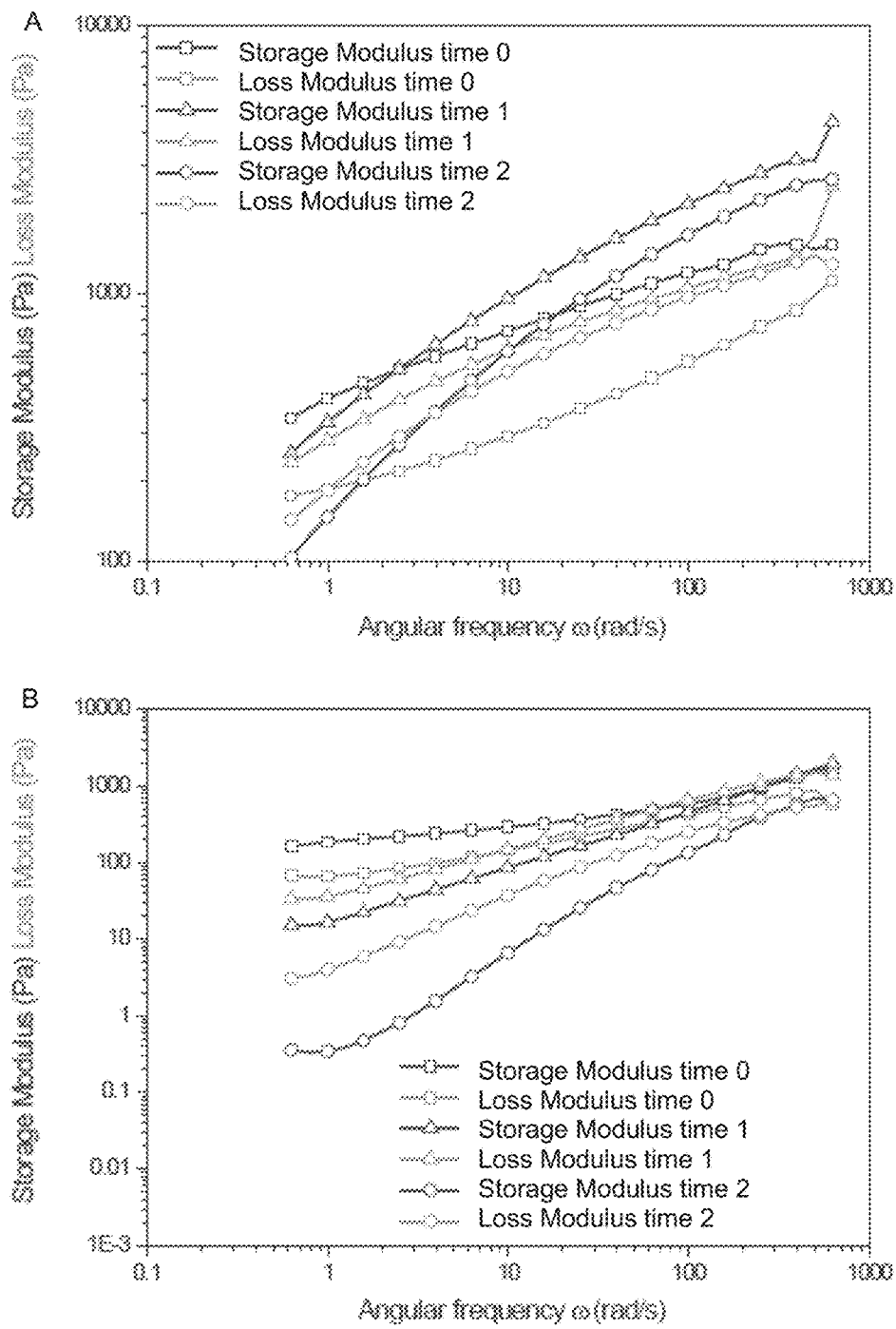
FIG. 10 show the frequency sweep of samples in A) Comparative Example 2 and B) Example 3 when mixed with P&G VT2510 premix (time 0=0 minutes, time 1=30 minutes and time 2=1 hour).

As shown in FIG. 10, the modulus of sample from Example 3 (FIG. 10B) when directly mixed with P&G VT2510 premix decreased as the time increased, reflecting that the sample gets less stiff as it dissolves and eventually the gel disintegrated with the loss modulus dominating. In contrast, the non-crosslinked sample from Comparative Example 2 (FIG. 10A) showed more solid like behaviour and was able to hold the different shear better. Although the storage modulus decreased with the time increase at a low angular frequency, the gel structures were well retained. Possible reason for the difference could be due to that the polyacids crosslinked with the PEG shells from individual polymer-silicone sample particle. This helped them to be flexible.

The rheology data are summarized in Table 3. The storage modulus (at frequency of 1 Hz) of the non-crosslinked samples (prepared by directly mixing the P&G VT2510 premix) were generally larger than the crosslinked samples. The tan delta values (at frequency of 1 Hz) of the Pluronic F108-silicone samples (Examples 1 and 2 and Comparative Example 1) were generally larger than those of the Pluronic F127-silicone samples (Examples 3 and 4 and Comparative Example 2). It is possible that using mixed Pluronics to prepare the Pluronic-silicone samples could modify the tan delta values as seen for Comparative Examples 5 and 6. The viscosities for all of the pluronics-silicone samples were similar at a low shear rate of 10. However, at high shear rate of 100, the viscosities of crosslinked samples were larger than that of the non-crosslinked samples.

TABLE 3

|  | Comp. Ex. 1 | Ex. 1 | Ex. 2 | Comp. Ex. 5 | Comp. Ex. 6 | Comp. Ex. 2 | Ex. 3 | Ex. 4 |
| --- | --- | --- | --- | --- | --- | --- | --- | --- |
| G' (Storage modulus) | 597 | 186 | 211 | 383 | 522 | 905 | 1422 | 734 |
| Yield stress | 20 | 10 | 12 | 10 | 10 | 10 | 10 | 8 |
| Tan delta | 0.74 | 0.92 | 0.98 | 0.37 | 0.49 | 0.39 | 0.27 | 0.37 |
| Viscosity ($\gamma = 10$) Pa · S | 3.29 | 3.53 | 2.91 | 3.10 | 4.07 | 3.89 | 4.91 | 3.70 |
| Viscosity ($\gamma = 100$) Pa.S | 1.27 | 1.43 | 1.80 | 0.93 | 0.79 | 1.46 | 2.12 | 2.01 |

Figure 11:
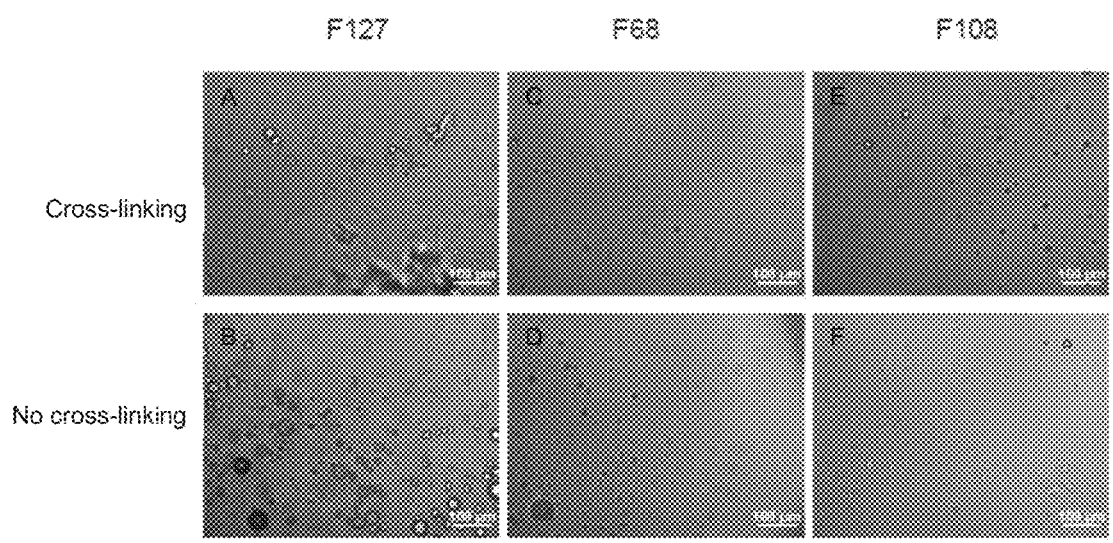
FIG. 11 show microscope images of the cross-linked and non-crosslinked samples after dissolution of A) Example 3; B) Comparative Example 2; C) Example 9; D) Comparative Example 7; E) Example 1 and F) Comparative Example 1.

The emulsion particle sizes after dissolution in the dissolution medium were compared across the various Pluronics samples. As can be seen in FIG. 11, the oil droplets of the Pluronics F127-silicone samples (FIG. 11A: Example 3 and FIG. 11B: Comparative Example 2) were larger than the Pluronics F108-silicone (FIG. 11E: Example 1 and FIG. 11F: Comparative Example 1) and the Pluronic F68-silicone samples (FIG. 11C: Example 9 and FIG. 11D: Comparative Example 7). This could be due to the higher content of hydrophobic polypropylene glycol units in Pluronics F127 that can form larger inner cores for the micelles.

INDUSTRIAL APPLICABILITY

The core-shell particle may be used to deliver the active agent to a desired site. The desired site may have a different pH other than an acidic pH so that the core-shell particle may disassemble to thereby release the active agent. The active agent may be present in the core of the core-shell particle and may be protected from the external environment by the shell.

The polyacidic polymer may form crosslinks with the biocompatible polymer so as to stabilise the core-shell particle to prevent premature or fast disassembly of the core-shell particle. Hence, the release of the active agent from the particle may be a sustained release over a period of time.

The core-shell particle may also be stable for a long period of time, as long as the pH where it is present in is not a pH that will cause disassembly of the particle.

The core-shell particle may thus be used as a delivery vehicle that can deliver a drug, an anti-microbial agent or a desired component to a surface or hair of a mammal. The core-shell particle may be ingestible or introduced into a body so as to deliver a drug or anti-microbial agent to a cell, tissue or organ of a mammal The core-shell particle may be added to a nutrient formulation, a skin care product, shampoo, conditioner or anti-foam products.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A core-shell particle comprising a polymer conjugate encapsulating an active agent, wherein said polymer conjugate comprises a biocompatible polymer and a polyacidic polymer.

2. The core-shell particle according to claim 1, wherein said biocompatible polymer is an amphiphilic polymer.

3. The core-shell particle according to claim 2, wherein said amphiphilic polymer is a block co-polymer comprising at least one hydrophobic polymer and at least one hydrophilic polymer block.

4. The core-shell particle according to claim 3, wherein said hydrophilic polymer block forms the shell of said particle and said hydrophobic polymer block forms the core of said particle.

5. The core-shell particle according to claim 1, wherein said biocompatible polymer comprises monomers selected from the group consisting of halogenated alkylene, ether, sulfonated ether, alkylene, ketone, sulfone, alkylene oxide, urethane, acetate, alcohol, carbonate, lactone, lactide, glycolide, ester, anhydride, acrylate, pyrrolidone, saccharide and combinations thereof; or preferably
said biocompatible polymer is selected from the group consisting of saturated or unsaturated carbon hydrogen chains, polyvinylchloride, polytetrafluoroethylene, polyethersulfone, polyethylene, polyetheretherketone, polysulfone, polypropylene, poly(ethylene glycol), poly(propylene glycol), polyurethanes, ethylene vinyl acetate copolymers, collagen, poly isobutylene, ethylene vinyl alcohol copolymers, polyethylene polycarbonate, poly-ε-caprolactone, polylactide, polyglycolide, carbomers, polyesters, polyethers, polyanhydrides, polyacrylates, polyvinyl acetates, polyvinyl pyrrolidones, polysaccharides, polyether, derivatives thereof and combinations thereof; or more preferably
said polysaccharide is selected from the group consisting of hyaluronic acid, hydroxyalkylcelluloses, carboxyalkylcelluloses, and derivatives thereof.

6. The core-shell particle according to claim 1, wherein said polyacidic polymer is selected from the group consisting of alginic acid, polysulfonamide, polypeptide, poly (carboxylic acid), polycarboxylate and combinations thereof; preferably said poly(carboxylic acid) is selected from the group consisting of poly(acrylic acid), poly(methacrylic acid), poly(2-ethylacrylic acid) and poly(2-propylacrylic acid); or more preferably said polypeptide is poly(aspartic acid) or poly(glutamic acid).

7. The core-shell particle of claim 3, wherein said hydrophobic polymer contains saturated or unsaturated carbon hydrogen chains; preferably said hydrophobic polymer is poly(propylene oxide) or poly(butyl methacrylate).

8. The core-shell particle of claim 2, wherein said amphiphilic polymer is a copolymer of poly(ethylene glycol)-poly(propylene glycol), a poloxamer, polyoxyethylene stearate or polysorbate.

9. The core-shell particle according to claim 1, wherein said active agent is a fluidic active agent or a particulate active agent; preferably said active agent is a fluidic active agent selected from silicone oil.

10. The core-shell particle of claim 1, wherein said active agent is encapsulated in the core of said particle.

11. The core-shell particle of claim 9, wherein said active agent is a particulate active agent selected from the group consisting of a therapeutic agent, a cosmetic agent and a cosmeceutical agent.

12. The core-shell particle of claim 1, wherein said particle has a particle size in the nano-size range or the micro-size range; preferably said particle size of said particle is from 10 nm to 10,000 nm or 200 nm to 5000 nm.

13. The core-shell particle according to claim 1, wherein said biocompatible polymer and said polyacidic polymer are in a respective polymers unit molar ratio of from 100:90 to 100:0.1.

14. The core-shell particle according to claim 1, wherein said active agent is loaded into said core at a loading concentration of from 1% to 80%.

15. The core-shell particle according to claim 1, wherein said biocompatible polymer and said polyacidic polymer cross-links at a crosslinking density of at least 5%, at least 10%, or at least 15%.

16. A process for forming a core-shell particle comprising a polymer conjugate encapsulating an active agent, wherein said polymer conjugate comprises a biocompatible polymer and a polyacidic polymer, the process comprising the steps of:
   a) providing a mixture comprising said biocompatible polymer or monomers thereof, said polyacidic polymer or salt thereof and said active agent in an acidic environment; and
   b) drying said mixture to obtain said core-shell particle.

17. The process according to claim 16, wherein providing step (a) comprises the step of homogenizing or emulsifying.

18. The process according to claim 16, wherein said drying step (b) comprises the step of heating, freeze drying, vacuum drying or spray drying.

19. The process according to claim 16, wherein said polyacidic polymer has a pKa value and said acidic environment is at a pH lower than said pKa value; preferably said pH is less than 7.5, less than 7, or about 6.

20. A delivery vehicle comprising the core-shell particle of claim 1, wherein said core-shell particle releases said active agent from said core when said particle is at a pH greater than the pKa of the polyacidic polymer;
   wherein said release of said active agent is sustained over a period of time.

21. A method for delivering an active agent to a desired site comprising the steps of:
   a) providing the core-shell particle of claim 1 in an acidic environment; and
   b) increasing the pH of said core-shell particle to thereby release and deliver said active agent;
   wherein said desired site is a hair or a surface of an animal.

22. The process according to claim 17, wherein said drying step (b) comprises the step of heating, freeze drying, vacuum drying or spray drying.

* * * * *